United States Patent [19]
Davis
[11] 4,444,763
[45] Apr. 24, 1984

[54] EXTRACTION OF AVOCADO OIL FROM AVOCADOS

[75] Inventor: Richard H. Davis, Valley Center, Calif.
[73] Assignee: Paino Avocado Company, Inc., Temecula, Calif.

[21] Appl. No.: 372,529
[22] Filed: Apr. 28, 1982
[51] Int. Cl.[3] .......... A61K 35/78
[52] U.S. Cl. .......... 424/195; 260/236.6
[58] Field of Search .......... 424/195; 260/236.6

[56] References Cited

PUBLICATIONS

E. F. Stenmetz, Codex Vegetabilis, 814, 1957.

*Primary Examiner*—Albert T. Meyers
*Assistant Examiner*—John W. Rollins, Jr.
*Attorney, Agent, or Firm*—Donald D. Mon

[57] ABSTRACT

A process for extracting raw and crude avocado oil from avocados with optimum yield and minimal chemical change in the oil. Raw avocado oil is extracted from ripe fruit following maceration, heating, addition of herbaceous silicious material, and pressure extraction. Crude avocado oil can be extracted from the remaining cake by refluxing with suitable solvents. The oil can further be refined by treatment in a diatomaceous earth filter.

13 Claims, 4 Drawing Figures

EXTRACTION OF AVOCADO OIL FROM AVOCADOS

FIELD OF THE INVENTION

This invention relates to extraction of avocado oil from avocados.

BACKGROUND OF THE INVENTION

Avocado oil comprises a significant proportion of the fruit of the avocado. The fruit of the avocado is generically referred to as "avocado" or as "an avocado" herein. This principally comprises avocado oil, seed, skin, fruit pulp and water. The oil itself has many uses, among them as an ingredient in salad dressings, in various foods, in cosmetics, and in the manufacture of soap. Various free fatty acids and vitamins are also found in the avocado.

The avocado itself, and avocado oil, have a widespread and growing appeal. This market appears to be limited only by availability of the fruit, and to a lesser extent by its cost. Because of the value of the land on which the avocado trees are grown, the lead time required to bring new trees into production, the care the trees require, their susceptibility to troublesome and disastrous diseases, especially viruses, and their susceptibility to the vagaries of the weather, it is a major decision whether to start a new orchard, and how to price, process and distribute the fruit and its by-products which can be produced.

One thing which can properly be stated is that whenever avocado oil is produced, there appears to be a market for it. In view of this fact, there have been many efforts made to extract the oil at least cost and in best quality. Depending on the market for fresh avocados and for processed avocado pulp in various forms such as frozen guacamole, the sale of avocado oil can often comprise an important source of income. Furthermore, it can be extracted from fruit which is of insufficient quality to sell as such, or which is in excess of market demands, thereby reducing at least some of the grower's risks.

Some problems with known extraction processes for avocado oil are (a) the use of hot water and enzymes to aid in the separation of pulp from the oil, adding to the processing problems because they tend to degrade the quality of the oil and cause dificulties in disposing of water process water, (b) boiling of the fruit to release the oil, resulting in low recovery and sometimes degraded oil, and (c) the use of centrifuges or of squeezing processes of low sophistication, which result in low oil yields.

It is an object of this invention to provide for efficient extraction of avocado oil at moderate temperatures, and for extracting raw oil with the addition only of herbaceous silicious material that is readily retained during extraction that facilitates the extraction of the oil.

It is another object of this invention to obtain from the process some of the values which are often discarded with the seeds and skins.

BRIEF DESCRIPTION OF THE INVENTION

This invention is accomplished with the use of ripe avocados, which are riper than "green" and "greener" than overripe, in which the avocado itself has an optimum content of avocado oil, and at least a minimized content of free fatty acids. Whole ripe avocados are charged into a macerator, where they are macerated by blades to relatively small pieces, and are heated, until the macerated, heated product is paste-like, although not necessarily without particles of seeds and skin.

This material is then intimately mixed and heated with particulate herbaceous silicious material such as rice hulls which aids in the separation of the oil from the solid material, this separation being accomplished with a filter press to produce "raw" avocado oil.

The heating processes are preferably accomplished in the presence of minimal oxygen, using radiant and/or conductive heat.

The above and other features of the invention will be fully understood from the following detailed description and the accompanying drawings, in which:

DETAILED DESCRIPTION OF THE INVENTION

Figure 1:
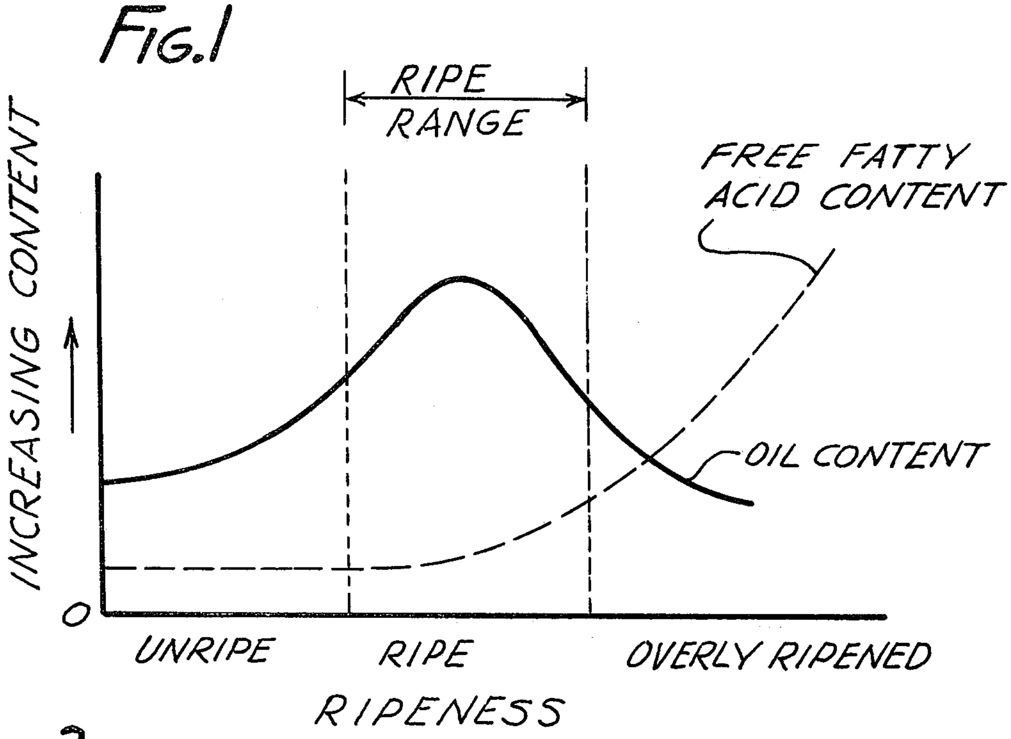
FIG. 1 is a graph showing the properties of an avocado.

The proper selection of avocados is quite important to obtaining the best yield. FIG. 1 is a graphical showing of two important properties of the avocado with reference to its ripeness. The solid line shows that in its unripened state the oil content is relatively low. As the avocado ripens, the oil content increases, and reaches a maximum with a range of ripeness. Thereafter, the oil content diminishes as the avocado becomes overly ripened.

The content of free fatty acids is shown by the dashed line. This content is relatively low in the unripe condition, and begins to increase substantially when the avocado nears the overly ripened condition. The free fatty acids dramatically increase as the avocado becomes increasingly overly ripened.

Ripening of the avocado after it is picked is a function of time and of temperature. Avocados are most frequently picked while still unripe, because they are then quite hard, and can withstand vigorous handling and processing.

The term "ripe" is used to designate an avocado whose pulp, while soft and readily edible without elasticity or hardness, still tends to retain its shape and a light green color. While the avocado will then yield somewhat to squeezing pressure, it is not soft or readily squeezed out of shape. Such a condition is usually associated with maximum palatability.

The term "overly ripe" is used to describe an avocado which is quite soft, whose bulk shape and pulp can readily be deformed, and which generally shows color and odor changes which are recognized as being beyond the limits of palatability and attractiveness.

The process of this invention is intended to extract avocado oil from ripe avocados, because the quality and quantity of oil are optimum in this range, and the free fatty acid content is at least minimized.

Figure 2:
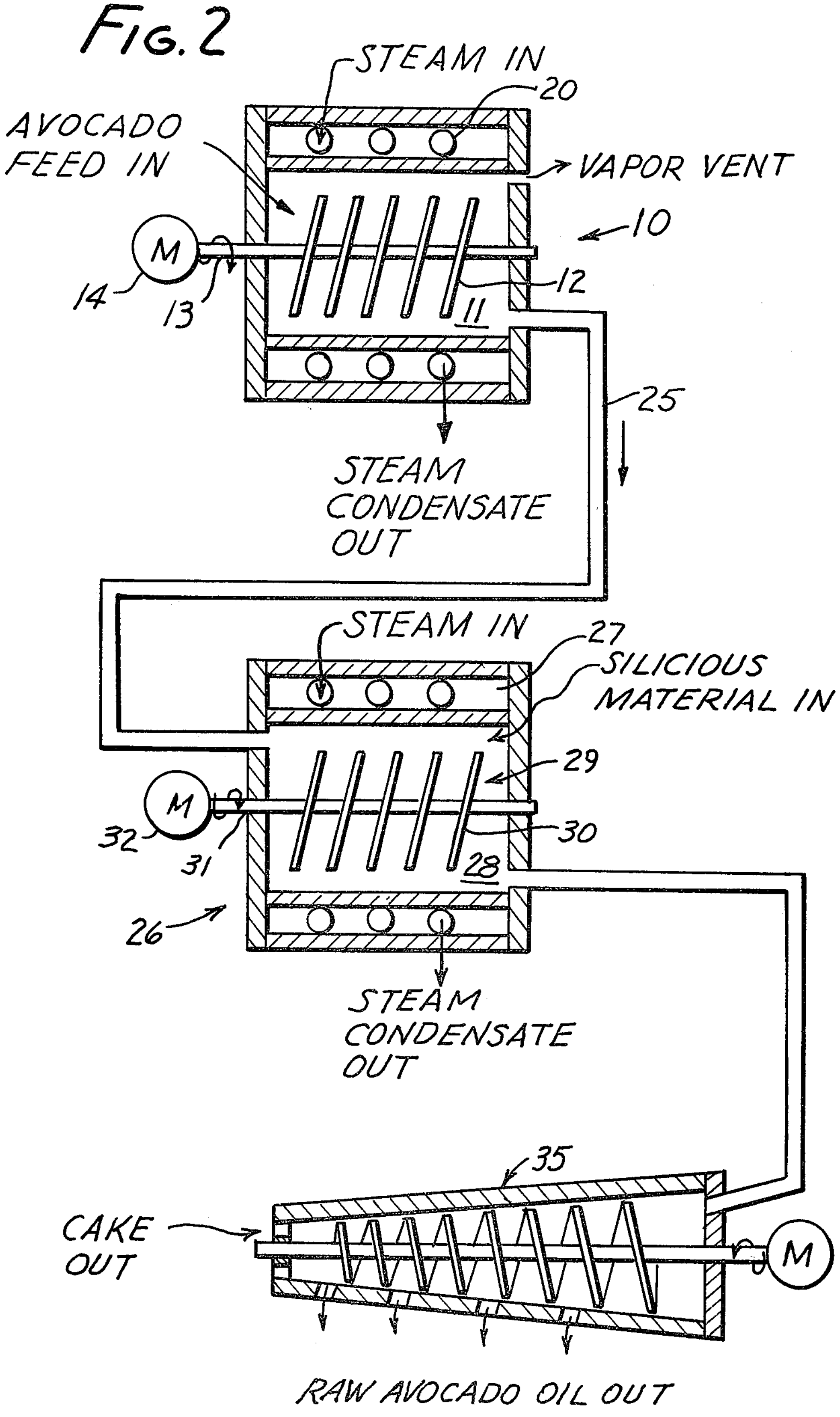
FIG. 2 is a process diagram for the major part of the processing.

The whole ripe avocados are charged into a macerator 10 (FIG. 2) having a chamber 11 in which blades 12 are rotated by a shaft 13 that is driven by motor 14. The objective of the blades is finely to chop the avocados, and to keep the chopped mass in stirring motion.

While the avocado mass is being stirred in the macerator, water is being extracted from it. A steam jacket 20 encircles the chamber to heat the chamber wall, thereby forming a source of radiant and/or conductive heat. The chamber is preferably maintained between 150°–200° F., which is high enough to drive off much of the water as vapor, but not so high as to degrade the oil. Preferably about 60% of the water content will be driven off in macerator 10, reducing the water content to about 7% to 10% by weight.

The macerator can be operated as a batch processor, although it can instead be operated on a continuous feed basis, by arranging the blades so they gradually advance the mass from a feed end to a discharge end. The avocado mass is preferably reasonably smooth in texture, although there will be pieces of seeds, and skin throughout the mass. The oil is primarily contained in the pulp.

The mass is carried by a conveyor 25 to a tempering box 26, which is maintained at a temperature between about 150°–200° F. A stem jacket 27 or other means to provide radiant and/or conductive heat to the mass, surrounds chamber 28 of the tempering box. Stirring means 29, such as blades 30 mounted to shaft 31 that is turned by a motor 32 stir the mass.

All heating is preferably done in regions which are at least restricted to the entry of oxygen. While this does not necessarily mean anaerobic conditions still it does mean the exclusion of oxygen to the maximum convenient extent so as to minimize oxidation of the product. For example, the water vapor that is driven off also tends to exclude oxygen. Exclusion of oxygen represses the tendency of the oil and other components of the mass to be oxidized.

Silicious material to facilitate expressing of the oil and expansion of the mass is added in this tempering operating. The presently preferred silicious material is rice hulls. It constitutes an example of a particulate fibrious herbaceous silicious material that has a relatively high silica content—namely between about 360 to 400 lbs. per ton of hulls (18% to 20% by weight). This is much higher than is found in most other herbaceous high silica materials, and for that reason is the preferred substance.

However, there are other useful high silica plants, and parts of plants, whose silica concentration runs between about 5%–20% silica by weight, and plant materials in this range are referred to as herbaceous silicious material. Rice (*Oriza Sativa*), especially its straw, is a useful and readily available material. Some grasses also have this property, for example wheat (*Triticum Aestivum*) and rye (*Secale Cereale*). Some plants which are not grasses also have this property, for example the sunflower (Helianthus Sp.) and horsetails (Equisetum Sp.). The silica will usually be concentrated in some specialized part of the plant, and this part will be used.

The point is, the addition of a herbaceous fibrous silicious plant material (having more than 5% $SiO_2$ by weight) to the mass will significantly improve the yield of avocado oil. Rice hulls are the most useful material because they are of a convenient size, are inexpensive and readily available, and have about the highest silica content of any readily available and suitable herbaceous material.

The mass is mechanically mixed in the macerator and or the tempering box, so that the rice hulls are uniformly distributed throughout, and sufficient residence time is allowed that the mass is uniformly warmed to a temperature between about 150° F. and 200° F., preferably about to 185° F. The amount of rice hulls to be added will be determined by trial and error to optimize the recovery and clarity of the recovered oil. Experiments have shown that about 160 pounds of rice hulls added to material in the tempering box which was derived from about 4000 pounds to whole avocados, is usually enough.

This mass is now pressed to extract the avocado oil. A simple screw press filter 35 is suitable. It is not necessary to resort to filter cloths or the like. A comparatively coarse screeen or series of parallel screen blades is adequate, and a good quality, quite clear raw avocado oil is expressed. The retained cake is dark brown, and includes the rice hulls and the avocado residues such as skin, seeds, and meal. Also there remains between about 5% and 10% avocado oil by weight. The herbaceous silicious material provides additional bulk for expression of the avocado oil, and a certain slickness that also seems to improve the expressing of the avocado oil. The cake is heavily pasty, and is readily retained by the press. Of course different types of presses can be used, but a screw press is a relatively inexpensive machine which is easily maintained, and is very acceptable for the purpose.

The resulting raw avocado oil can be cleaned up by finer filtration to remove small entrained particulates, and will contain all of its vitamins and free fatty acids. If it is desired to remove the vitamins and free fatty acids, the raw oil can be passed through a diatomaceous earth filter which will remove them. Such a filter would also remove particulates. The vitamins and free fatty acids remain in the diatomaceous earth, from which they can later be reclaimed.

Figure 3:
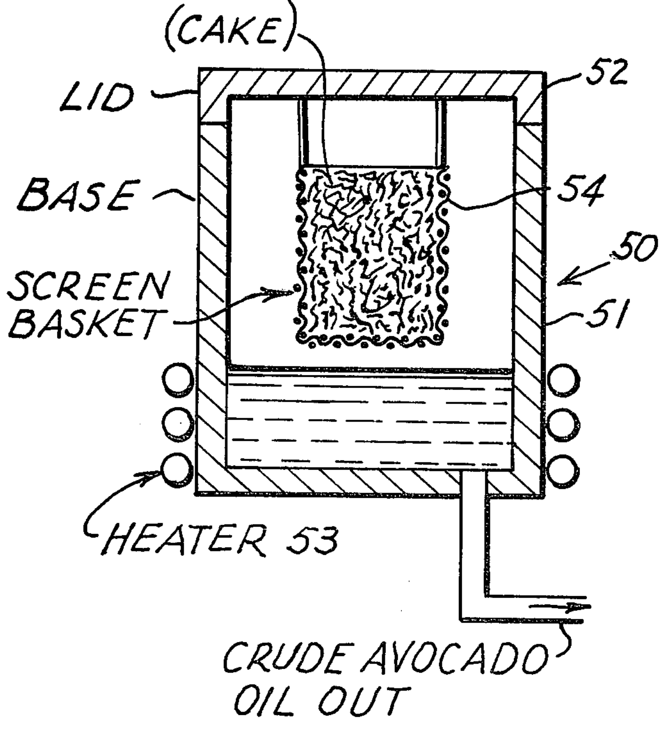
FIGS. 3 and 4 are process diagrams showing optional secondary processes.

While the cake from the screw press is directly useful for such purposes as animal feed, the residual avocado oil, vitamins, and free fatty acids may sometimes have sufficient value to merit extraction from the cake. FIG. 3 shows a technique for such an extraction. A retort 50 has a kettle base 51, a lid 52, heater coils 53, and a perforated basket 54. The basket is filled with the cake and suspended in the closed retort. A suitable solvent is placed in the retort and heated so as to evaporate and reflux through the cake. As a consequence, after sufficient refluxing the avocado oil, vitamins and free fatty acids will be leached from the cake, and will collect in the base, from which they are drained. The solvent can be recovered from the oil by conventional means such as by applying sufficient heat to drive off the volatile solvent.

The solvent to be used should be safe for foods, because the avocado oil may ultimately be consumed. For this purpose, methylene chloride is a preferred substance. It is generally recognized as safe ("grass"), and can be removed at about 150° C.

The avocado oil recovered in this leaching process is sometimes referred to as "crude" avocado oil. As with any secondary oil recovery, the quality of the crude oil will not be as high as that of the raw oil from the virgin press, but each has its uses, and the two oils may even be combined to form a useful product.

Figure 4:
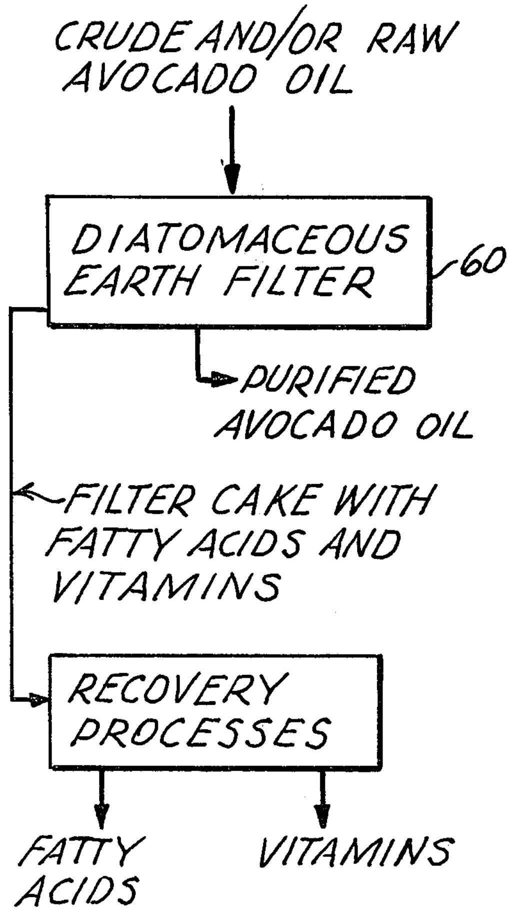

FIG. 4 shows the previously described filtration of avocado oil in a diatomaceous earth filter 60. The resulting oil (from raw and/or crude avocado oil) may be termed "purified" oil. The cake can be subjected to tertiary processes to recover vitamins and/or free fatty acids. Such tertiary recovery forms no part of this invention, and is therefore not discussed here.

A very useful product is the raw vitamin oil, filtered free of particulates in a fine filter.

This invention thereby provides an improved process for the recovery of avocado oil, both raw and crude, using simple equipment, and causing minimal change to the natural properties of the oil.

This invention is not to be limited to the embodiments shown in the drawings and described in the description, which are given by way of example and not of limitation, but only in accordance with the scope of the appended claims.

I claim:

1. A process for extracting avocado oil from avocados, comprising:

a. selecting ripe whole avocados;

b. macerating and heating said avocados to reduce them to a fine consistency and removing a substantial portion of their water content;

c. adding herbaceous silicious plant material, having a silica content in excess of about 5% weight, to the product of step b, in such proportion as significantly to improve the recovery and clarity of avocado oil as compared with identical processing without said herbaceous plant material, and continuing to heat it while mixing in said plant material to form a substantially uniform mass; and d. pressing the mass produced in step c to extract raw avocado oil from it, the temperature to which the avocados and plant material is heated, being sufficiently elevated to encourage the vaporization of water, but insufficiently elevated to significantly degrade the avocado oil.

2. A process according to claim 1 in which the heating in b and c is provided by radiant and/or by conductive means.

3. A process according to claim 2 in which oxygen is substantially excluded from the process during steps b and c.

4. A process according to claim 1 in which steps b and c are conducted at temperatures between about 150° and 200° F.

5. A process according to claim 1 in which said plant material is derived from the plant Oriza Sativa.

6. A process according to claim 5 in which said plant material is rice hulls.

7. A process according to claim 6 in which steps b and c are conducted at temperatures between about 150° and 200° F.

8. A process according to claim 1 in which step d is conducted in a screw press.

9. A process according to claim 1 in which step d produces a residue cake, and in which said cake is leached in a solvent in which avocado oil is soluble, and which is safe for foods, said solvent being thereafter removed from said oil, thereby to produce crude avocado oil.

10. A process according to claim 8 in which said solvent is methylene chloride.

11. A process according to claim 9 in which said crude avocado oil is passed through a diatomaceous earth filter to remove vitamins and free fatty acids therefrom.

12. A process according to claim 9 in which said raw avocado oil is also passed through said diatomaceous earth filter to remove vitamins and free fatty acids therefrom, said raw and crude avocado oils being mixed and simultaneously passed through said filter.

13. A process according to claim 1 in which said raw avocado oil is passed through a diatomaceous earth filter to remove vitamins and free fatty acids therefrom.

* * * * *